US012754331B2

(12) United States Patent
Bollenbeck et al.

(10) Patent No.: US 12,754,331 B2
(45) Date of Patent: Oct. 6, 2026

(54) TIMING PICKOFF CIRCUIT

(71) Applicant: Siemens Medical Solutions USA, Inc., Malvern, PA (US)

(72) Inventors: Jan Bollenbeck, Eggolsheim (DE); Martin Judenhofer, Knoxville, TN (US); Nan Zhang, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 384 days.

(21) Appl. No.: 18/664,866

(22) Filed: May 15, 2024

(65) Prior Publication Data

US 2025/0355122 A1 Nov. 20, 2025

(51) Int. Cl.

| | |
|---|---|
| ***G01T 1/20*** | (2006.01) |
| ***A61B 6/03*** | (2006.01) |
| ***A61B 6/42*** | (2024.01) |
| ***H03F 3/68*** | (2006.01) |

(52) U.S. Cl.

CPC .......... *G01T 1/20182* (2020.05); *A61B 6/037* (2013.01); *A61B 6/4266* (2013.01); *H03F 3/68* (2013.01)

(58) Field of Classification Search

CPC ... G01T 1/20182; G01T 1/2985; A61B 6/037; A61B 6/4266; A61B 6/032; A61B 6/4258; H03F 3/68

See application file for complete search history.

(56) References Cited

U.S. PATENT DOCUMENTS

| | | | | |
|---|---|---|---|---|
| 5,376,834 | A * | 12/1994 | Carobolante ............. | G05F 1/46 327/341 |
| 9,086,492 | B2 | 7/2015 | Zhang et al. | |
| 10,557,947 | B1 * | 2/2020 | Zhang .................. | G01R 33/481 |
| 2018/0038966 | A1 * | 2/2018 | Fu ....................... | G01T 1/20184 |
| 2018/0372822 | A1 * | 12/2018 | Kim ..................... | G01R 33/481 |
| 2020/0041665 | A1 | 2/2020 | Mintzer et al. | |
| 2022/0397688 | A1 * | 12/2022 | Qiang .................... | A61B 6/037 |

OTHER PUBLICATIONS

Bauer, Florian et al., "Dynode-Timing Method for PET Block Detectors", IEEE Transactions on Nuclear Science, vol. 55, No. 1, Feb. 2008, Digital Object Identifier 10.1109/TNS.2007.910879, (pp. 451-456, 7 total pages).

* cited by examiner

*Primary Examiner* — Casey Bryant
*Assistant Examiner* — Gisselle M Gutierrez

(57) ABSTRACT

Systems and methods include a plurality of electrical transducers, each of the plurality of electrical transducers comprising an anode and a cathode, a plurality of common-base amplifiers, an input of each of the plurality of common-base amplifiers connected to a cathode of a respective one of the plurality of electrical transducers, a summation point to which an output of each of the plurality of common-base amplifiers is connected, and an amplifier, wherein an input of the amplifier is connected to the summation point.

19 Claims, 7 Drawing Sheets

TIMING PICKOFF CIRCUIT

BACKGROUND

According to conventional positron-emission-tomography (PET) imaging, a radionuclide tracer is introduced into a patient body. Radioactive decay of the tracer generates positrons which eventually encounter electrons and are annihilated thereby. An annihilation produces two photons which travel in approximately opposite directions.

A ring of detectors surrounding the body detects the photons, identifies "coincidences" based thereon, and reconstructs PET images based on the identified coincidences. A coincidence is identified when two photons arrive at two detector elements within a particular coincidence time window. Because the two "coincident" photons travel in approximately opposite directions, the locations of the two detector elements determine a Line-of-Response (LOR) along which an annihilation may have occurred. Time-of-flight (TOF) PET additionally measures the difference between the detection times of the two photons arising from the annihilation. This difference may be used to estimate a particular position along the LOR at which the annihilation event occurred. Both coincidence detection and TOF measurements require extremely accurate and consistent determination of photon arrival times.

Arrival of a photon at a detector element causes a transducer to generate an electrical signal, or pulse. Generally, a photon arrival time (i.e., "event time") is identified as a time at which the generated pulse crosses a threshold voltage. A coincidence is identified when the event times determined from two generated pulses are within the coincidence time window.

Timing pickoff circuits are used to determine event times. Some conventional timing pickoff circuits determine event times based on a signal which combines the output pulses of several adjacent transducers. The combined signal exhibits low amplitudes, a low signal-to-noise ratio and a slow leading edge, all of which contribute to a degraded arrival time resolution. Some circuits amplify the combined signal using multi-stage high-gain, low-noise RF-amplifiers, which alleviates but does not satisfactorily address the above issues.

Systems are desired to efficiently improve the time-resolving characteristics of a timing signal consisting of the combined output of several transducers.

DETAILED DESCRIPTION

The following description is provided to enable any person in the art to make and use the described embodiments. Various modifications, however, will remain apparent to those in the art.

The present inventors have discovered that the performance of existing timing pickoff circuits for PET detectors is limited due to power mismatching (i.e., both impedance mismatching and noise mismatching) between the very low (e.g., a few ohms) "source impedance" of a transducer array (e.g., several transducers connected in parallel) disposed in a "common cathode" arrangement and higher (e.g., 50 ohm) input impedance of the following gain stage. Impedance mismatching causes most of the timing signal to be "self-absorbed" in the transducer array. Consequently, only a small fraction of the signal is output, and this small fraction exhibits low signal amplitude and poor signal-to-noise ratio. In the high frequency signal region, the mismatch is particularly troublesome since the high frequency components of the timing signals are crucial for accurate PET timing pickoff.

According to some embodiments a "buffer stage" is added to the cathode output of each transducer of an array of transducers (e.g., 4×4 array). outputs of the buffer stages are summed together to form a single timing signal. This timing signal is sent to a leading edge discriminator (LED) circuit and a time-to-digital converter (TDC) to resolve event times based on the timing signal.

The buffer stages comprise impedance transformers such as but not limited to common-base amplifiers. A common-base amplifier exhibits a low input impedance to advantageously enable short transducer response-duration times. The low input impedance also greatly reduces self-absorption of the transducer output signals within the transducer array. The summed timing signal thereby exhibits higher signal amplitude, improved signal-to-noise ratio and a faster pulse slope than conventional designs. The improved timing signals provide improved PET detector timing pickoff accuracy and finer PET coincidence timing resolution in order to improve PET TOF event localization.

The common-base amplifier has a high output impedance and acts as a high-impedance current source. Due to the high output impedance, the collector currents of the common-base amplifiers are amenable to being summed to generate a timing signal.

Moreover, the buffer stages substantially isolate each transducer of the transducer array from one another to prevent crosstalk and signal self-absorption within the detector array. The isolation also prevents the pulses from being reflected back and forth between the impedance discontinuities of the connection network, which would distort the pulse shape.

Figure 1A:
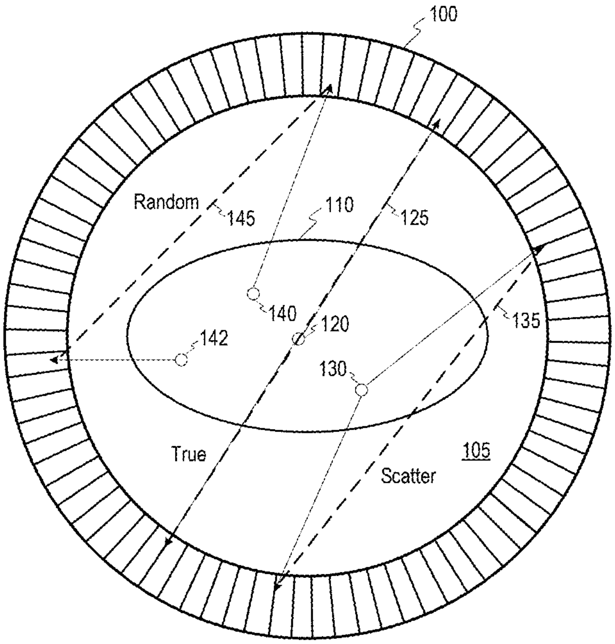
FIGS. 1A and 1B illustrate detection of coincidences according to some embodiments.
Figure 1B:
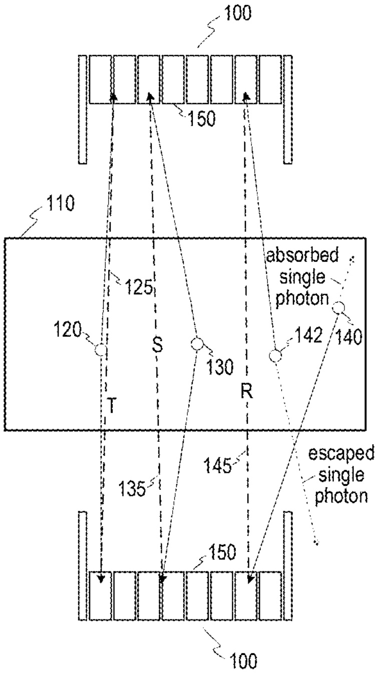

FIG. 1A and FIG. 1B illustrate detection of coincidences within a PET scanner according to some embodiments. FIG. 1A is a transaxial view of bore 105 of PET scanner detector ring 100 and imaging subject 110 disposed therein. Imaging subject 110 may comprise a human body, a phantom, or any other suitable subject. FIG. 1B is an axial view of detector ring 100 and body 110 of FIG. 1A. Detector ring 100 is composed of an arbitrary number (eight in this example) of adjacent and coaxial rings of detectors 150 in the illustrated example. Each detector 150, also known as a detector block, may comprise any number of crystals (i.e., detector elements) and transducers.

The crystals may comprise lutetium oxyorthosilicate (LSO), lutetium-yttrium oxyorthosilicate (LYSO), or any other suitable materials that are or become known. The crystals create light photons in response to receiving 511 keV photons and in response to receiving the emitted background radiation. The electrical transducers, or photosensors, convert these light photons to electrical signals, sometimes referred to herein as pulses. According to some embodiments, the electrical transducers may comprise silicon photomultipliers (SiPMs) or photomultiplier tubes (PMTs).

Annihilations 120, 130, 140 and 142 are assumed to occur at various locations within subject 110. As described above, an injected tracer generates positrons which are annihilated by electrons to produce two 511 keV photons which travel in approximately opposite directions. Each of annihilations 120, 130, 140 and 142 results in the detection of a coincidence. True coincidences represent valid image data, while scatter and random coincidences represent noise associated with incorrect event position information.

A coincidence is identified when two photons arrive at two detector crystals within a short time window (i.e., the coincidence time window), thereby indicating that the two photons arose from the same positron annihilation. The locations of the two detector crystals determine an LOR along which an annihilation may have occurred, and the difference between the detection times of the two photons can be used to estimate a particular position along the LOR at which the annihilation occurred.

Annihilation 120 is associated with a true coincidence because annihilation 120 resulted in two photons which were detected within the coincidence time window and because the position of annihilation 120 lies on LOR 125 connecting the positions of the crystals at which the two photons were received.

Annihilation 130 is associated with a scatter coincidence because, even though the two photons resulting from annihilation 130 were detected within the coincidence time window, the position of annihilation 130 does not lie on LOR 135 connecting the two photon positions. This may be due to Compton (i.e., inelastic) or Coherent (i.e., elastic) scatter resulting in a change of direction of at least one of the two annihilation photons within subject 110.

Annihilations 140 and 142 are two separate annihilations which result in detection of a random coincidence. In the present example, one of the photons generated by annihilation 140 is absorbed in body 210 and one of the photons generated by annihilation 142 escapes detection by any detector 150 of detector ring 100. The remaining photons happen to be detected within the coincidence time window, even though no annihilation occurred on LOR 145 connecting the positions at which the coincident photons were received.

The detected coincidences may be stored as raw (i.e., list-mode) data and/or sinograms. List-mode data may represent each coincidence using data specifying a LOR between two crystals, the time at which each photon of the annihilation reached each crystal, the photon energies, etc. A sinogram is a data array of the angle versus the displacement of the LORs of each detected coincidence. A sinogram includes one row containing the LOR for a particular azimuthal angle φ. Each of these rows corresponds to a one-dimensional parallel projection of the tracer distribution at a different coordinate. A sinogram stores the location of the LOR of each coincidence such that all the LORs passing through a single point in the volume trace a sinusoid curve in the sinogram. Since only the true unscattered coincidences indicate locations of annihilations, random coincidences and scatter coincidences are often subtracted from or otherwise used to correct acquired list-mode data or sinograms during reconstruction of a PET image based thereon.

Figure 2:
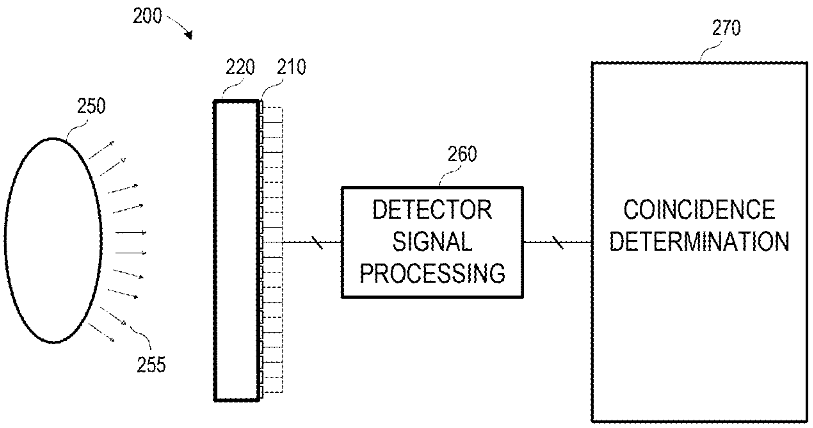
FIG. 2 is a block diagram of a coincidence determination system according to some embodiments.

FIG. 2 illustrates PET detector ring portion 200 of a PET scanner according to some embodiments. Detector ring portion 200 includes transducers 210 and scintillator 220. Detector ring portion 200 may consist of one or more detector blocks.

Detector ring portion 200 is positioned to detect gamma photons 255 emitted from volume 250. Systems for facilitating the emission of gamma photons from a volume are known in the art, and in particular with respect to the PET imaging described herein. A gamma ray penetrates into scintillator 220 and interacts therewith to generate light photons. As the light photons approach a given transducer 210, a signal is induced at the given transducer 210 and at its neighboring transducers 210. Embodiments are not limited to scintillator-based detectors. For example, direct conversion detectors (e.g., CZT and TIBr) which generate electrical signals based on received gamma photons may also be used in conjunction with some embodiments.

Detector signal processing unit 260 receives the electrical signals (i.e., pulses) generated by each of transducers 210. Detector signal processing unit 260 performs signal processing to, for example, reject invalid pulses, perform pulse unpiling, determine event timing and determine event location. Detector signal processing unit 260 may include a timing pickoff circuit as described herein to generate an improved timing signal from the outputs of several adjacent transducers 210, and may determine event times and locations based thereon. Coincidence determination unit 270 receives all event times and locations determined by unit 260 and identifies a coincidence for each pair of event times which fall within a coincidence time window. Coincidence determination unit 270 may determine a LoR for each coincidence based on the event locations and may also determine TOF information for each coincidence. Detector signal processing unit 260 and coincidence determination unit 270 may perform any suitable functions and exhibit any suitable implementations.

Figure 3:
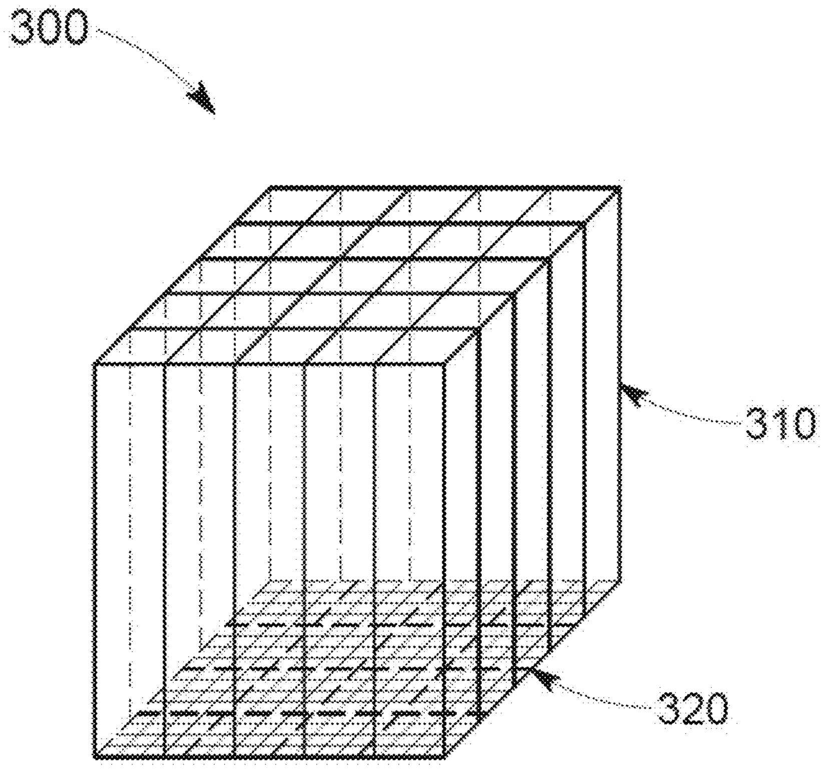
FIG. 3 illustrates a detector block according to some embodiments.

FIG. 3 illustrates detector block 300 according to some embodiments. Block 300 includes 5×5 array 310 of scintillation crystals (e.g., LSO). Array 310 is coupled to 4×4 array 320 of transducers. Each transducer of array 310 may comprise a 4×4 array of transducers (e.g., SiPM devices). According to some embodiments, each of the latter 4×4 arrays outputs a single timing signal which is formed by coupling the cathodes of the transducers as described herein. Embodiments are not limited to the arrangement, structure and array sizes of detector block 300.

Figure 4:
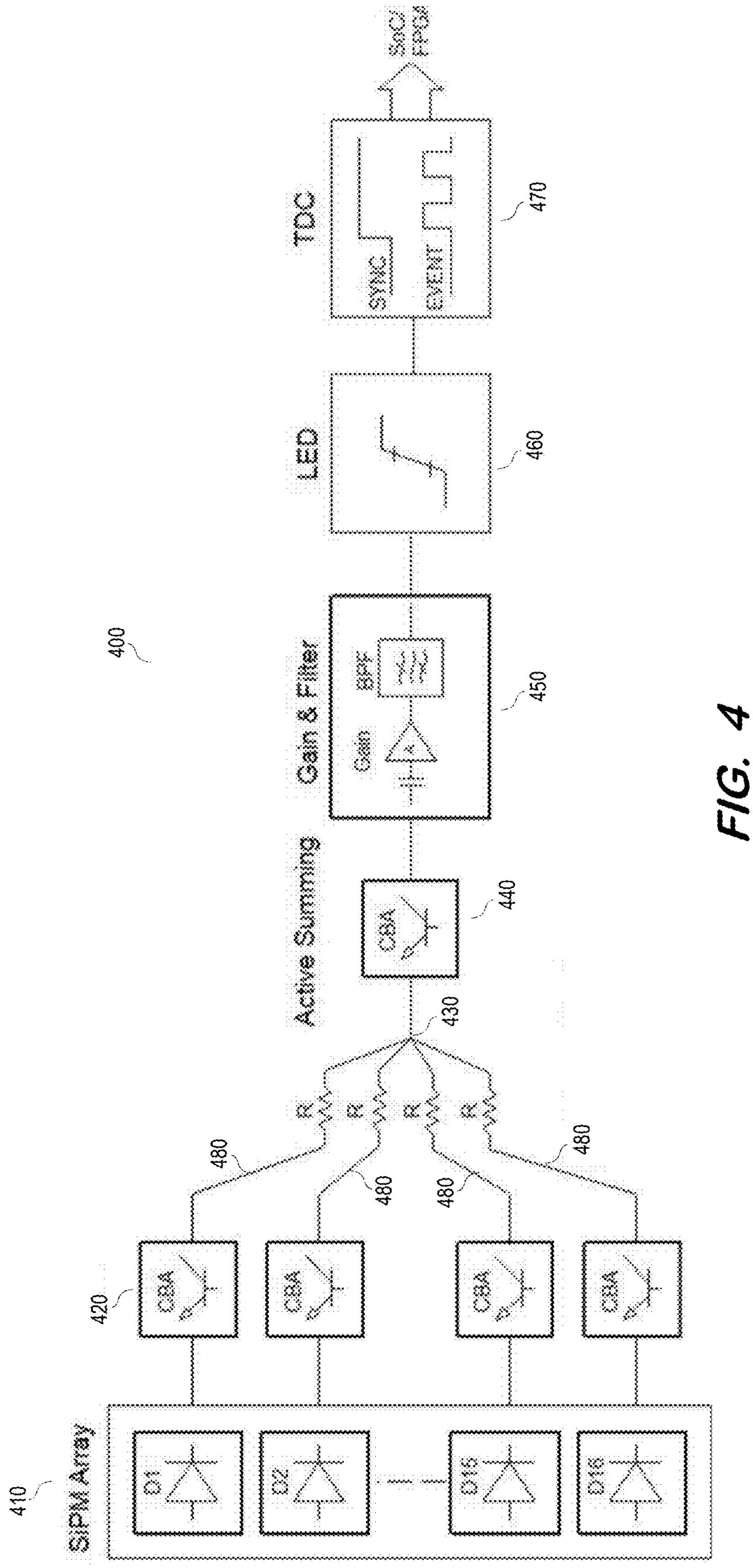
FIG. 4 is a block diagram of a timing pickoff circuit according to some embodiments.

FIG. 4 is a block diagram of timing pickoff circuit 400 according to some embodiments. Circuit 400 shows array 410 of SiPM transducers D1-D16. Array 410 may comprise transducers within a detector block as described with respect to FIG. 3. Array 410 may consist of any number and/or type of transducers.

The cathodes of each transducer D1-D16 are connected to an input of a respective one of common-base amplifiers 420. Common-base amplifiers 420 may be implemented as is or becomes known. Common-gate field-effect transistor amplifiers may alternatively be used in some embodiments. The term "common-base amplifier" as used herein encompasses both types of transistor amplifiers.

Ideally, the input impedance of each common-base amplifier 420 should be purely resistive. The input resistance depends on the present transistor collector DC-current (i.e., $r_{in}=U_{TH}/I_C$; $U_{TH}$: Thermal Voltage) and should be as low as possible. According to some embodiments, a common-base amplifier is implemented using a small footprint, low noise, high-speed silicon NPN RF bipolar transistor, or a dedicated custom application-specific integrated circuit (ASIC). The collector terminal of each common-base amplifier transistor acts like a high-impedance current source. Connecting several collector terminals in parallel can be used in some embodiments to form the "current summing" at the device connected thereto.

The output of each of common-base amplifiers 420 is connected to the input of a transmission line 480. All transmission lines 480 have the same characteristic impedance $Z_0$ (e.g., 50R) and the same length. The output of each transmission line 480 is connected to a port of a serial resistor R. The other port of each resistor R is directly connected to summing node 430. The values of resistors R are equal and chosen to match the interface impedances to the transmission line characteristic impedance $Z_0$.

Embodiments are not limited to a single resistor between the output of a transmission line 480 and summing node 430. Each resistor R may be replaced with a more complex network of resistive and/or capacitive components, for example. A more complex network may compensate for undesirable amplitude frequency responses, optimize the pulse shape/duration, and/or reduce pulse reflections at impedance discontinuities (i.e., pulse shape distortions). In some embodiments, each resistor R is replaced with a resistor in parallel with a capacitor.

Summing node 430 is connected to an input of active summing block 440. Active summing block 440 may be implemented by a common-base amplifier. The common-base amplifier of block 440 may be identical to amplifiers 420, but embodiments are not limited thereto. Active summing block 440 may provide defined resistive loads for each of amplifiers 420 and may decouple each of amplifiers 420 from one another. These characteristics provide stability and improved frequency response (i.e., greater bandwidth, flatter response). This is particularly advantageous in a case where common base amplifiers 420 are spatially separated from summing amplifier 440. Since the input impedance of common base amplifiers 420 is very low, it may be advantageous to place them individually as close as possible to their corresponding SiPM transducers to prevent unwanted impedance transformation due to mismatched transmission lines.

The output of active summing block 440 is connected to gain and filter circuit 450. Gain and filter circuit 450 may implement any design that is or becomes known, and outputs a signal to LED 460. LED 460 identifies leading edges of valid pulses and provides TDC 470 with an indication of a trigger time at which a leading edge crossed a threshold voltage. TDC 470 converts the indication to an event time (e.g., a value of a counter to which all detector blocks are synchronized). The event time is associated with arrival of a photon at a detector element coupled to array 410 and may be used to identify coincidences as described above. LED 460 and TDC 470 may be considered timing discrimination circuitry, but embodiments are not limited thereto.

Figure 5:
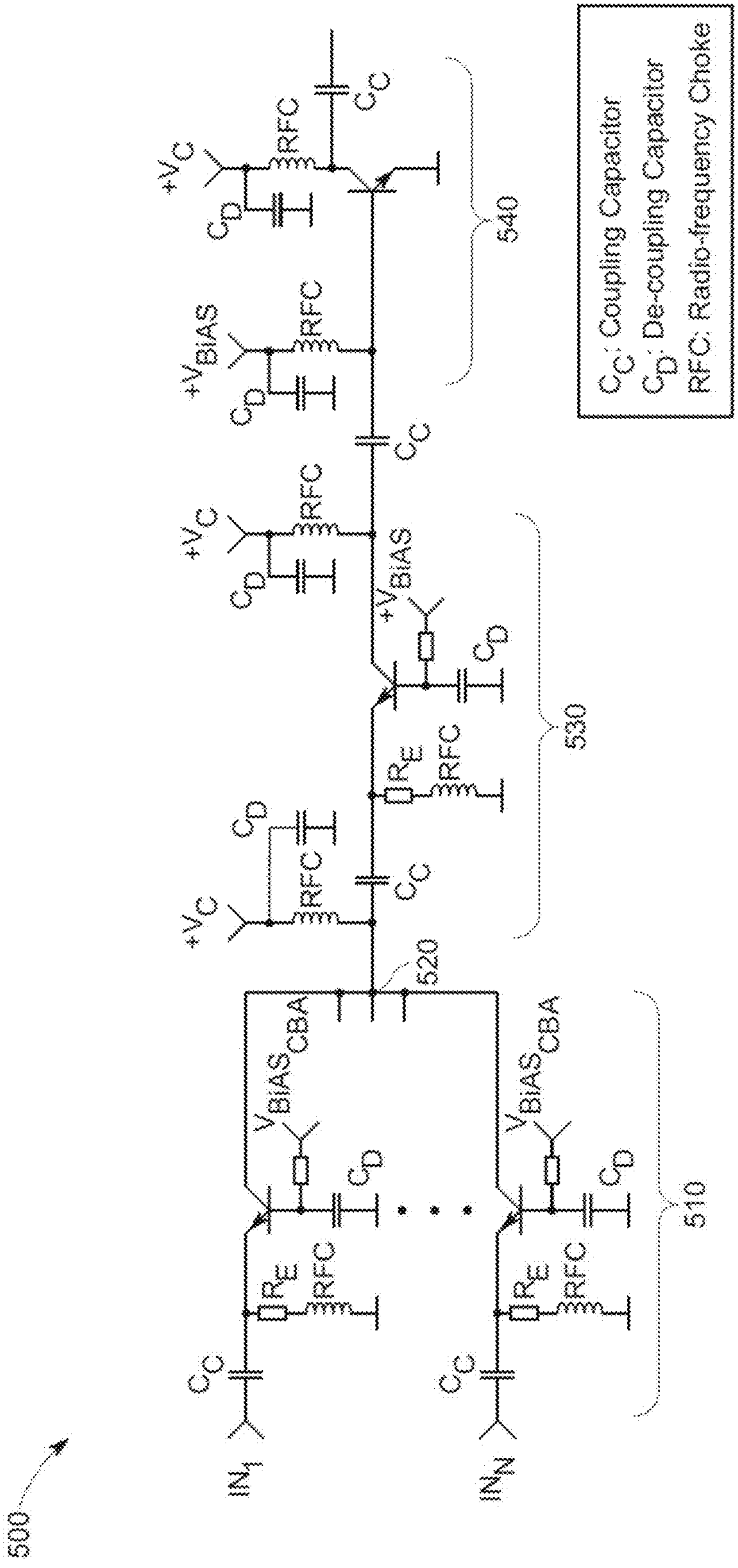
FIG. 5 is a schematic diagram of components of a timing pickoff circuit according to some embodiments.

FIG. 5 is a schematic diagram of components 500 of a timing pickoff circuit according to some embodiments. Components 500 may comprise an implementation of components of circuit 400 according to some embodiments. Components 500 receive input signals $In_1$ to $In_n$ from N electrical transducers such as SiPM devices. Input signals $In_1$ to $In_n$ are the cathode outputs of the SiPM devices according to some embodiments. Each input signal $In_1$ to $In_n$ is connected to an input of a respective one of N common-base amplifiers 510.

The output of each of the N common-base amplifiers 510 is connected to summing node 520 to sum the outputs. When common base amplifiers 510 are spatially separated from summing amplifier 440, this connection might be implemented by means of transmission lines and matching resistors. Active summing block 530 is connected to summing node 520 as described with respect to FIG. 4. The output of active summing block 530 is connected to gain circuit 540 to amplify the combined signal output by summing block 530.

Figure 6:
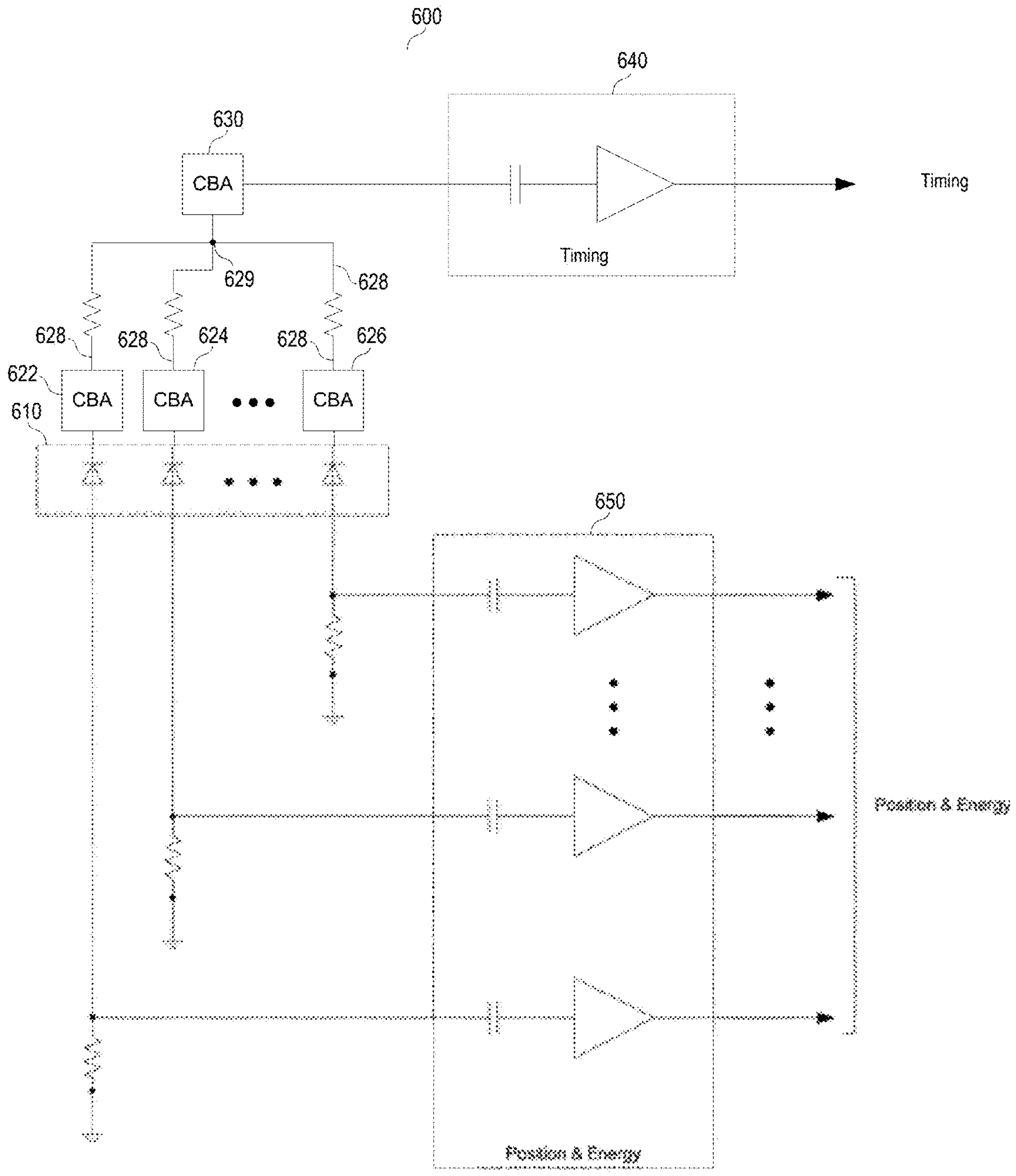
FIG. 6 is a schematic diagram of components of a timing pickoff circuit according to some embodiments.

FIG. 6 is a schematic diagram of components 600 of a timing pickoff circuit according to some embodiments. Components 500 may comprise an implementation of components 600 according to some embodiments but embodiments are not limited thereto.

Components 600 include SiPM transducers 610, depicted as diodes. The cathode of each transducer 610 is connected to a respective one of common-base amplifiers 622, 624, 626. The output of each of common-base amplifiers 622, 624, 626 is coupled, via transmission lines 628 and matching resistors, to one another and to summing point 629. The input of common-base amplifier 630 is also connected to summing point 629 and the output of common-base amplifier 630 is in turn coupled to timing signal gain circuit 640. Circuit 640 outputs a signal which may be used for event detection and timing.

The anodes of each of transducers 610 are coupled to respective gain circuits of position and energy gain circuits 650. Each of the respective gain circuits of position and energy gain circuits 650 outputs a signal which corresponds to the transducer to which the gain circuit is connected. The output signals are used to determine event locations and energies.

Figure 7:
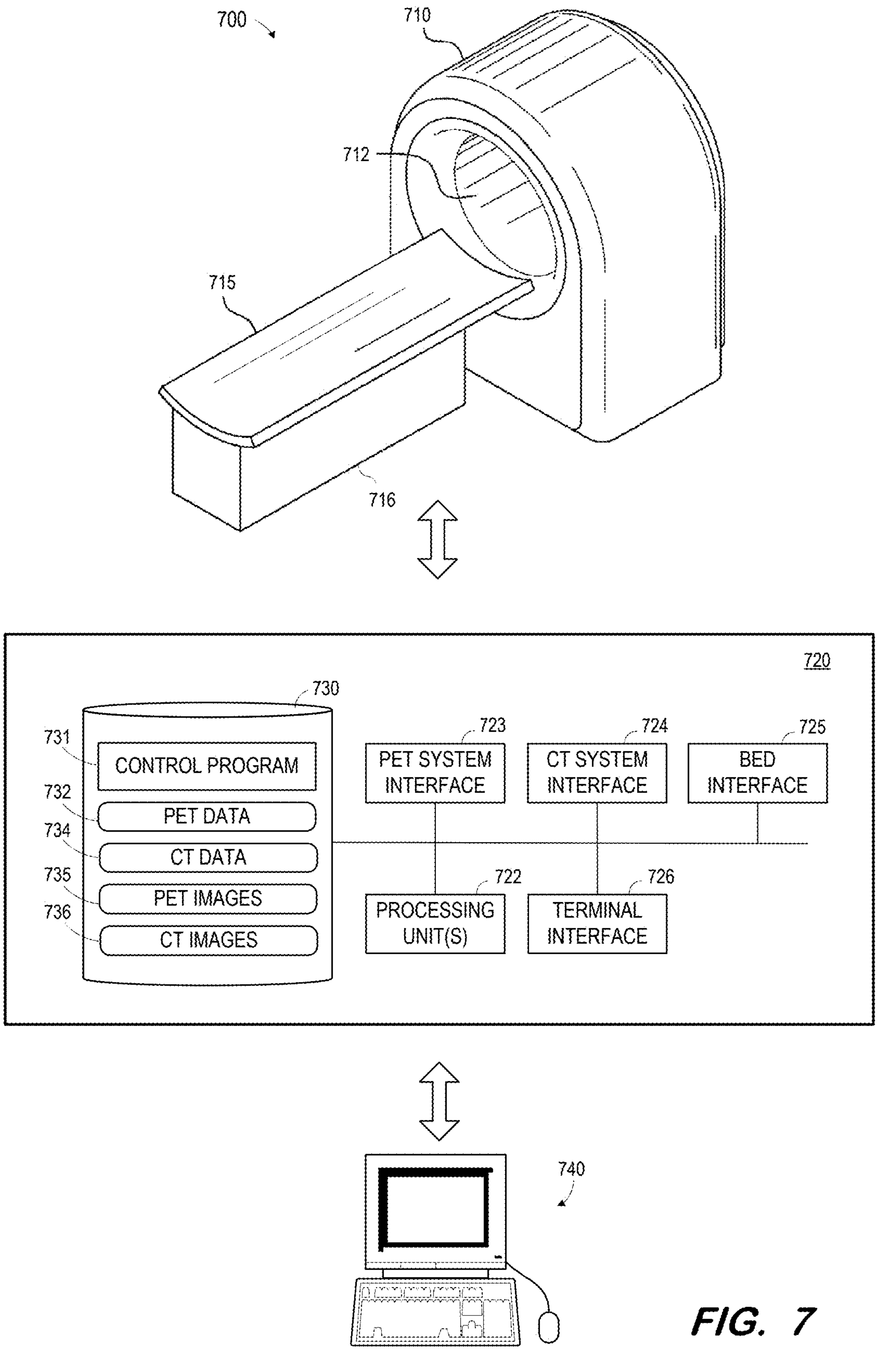
FIG. 7 is a block diagram of a PET-CT imaging system according to some embodiments.

FIG. 7 illustrates PET/CT imaging system 700 to execute one or more of the processes described herein. Embodiments are not limited to system 700, to a multi-modality imaging system, or to an imaging system.

System 700 includes gantry 710 defining bore 712. As is known in the art, gantry 710 houses PET imaging components for acquiring PET image data and CT imaging components for acquiring CT image data. The CT imaging components may include one or more x-ray tubes and one or more corresponding x-ray detectors as is known in the art. The PET imaging components may include any number or type of detectors in any configuration as is known in the art. Pulses generated by such detectors may be processed by analog and digital components as described herein to generate timing signals for discrimination of valid pulses and determination of event times.

Bed 715 and base 716 are operable to move a patient lying on bed 715 into and out of bore 712 before, during and after imaging. In some embodiments, bed 715 is configured to translate over base 716 and, in other embodiments, base 716 is movable along with or alternatively from bed 715.

Movement of a patient into and out of bore 712 may allow scanning of the patient using the CT imaging elements and the PET imaging elements of gantry 710. Bed 715 and base 716 may provide continuous bed motion and/or step-and-shoot motion during such scanning according to some embodiments.

Control system 720 may comprise any general-purpose or dedicated computing system. Accordingly, control system 720 includes one or more processing units 722 (e.g., processors, processor cores, processor threads) configured to execute program code to cause system 720 to acquire image data and generate images therefrom, and storage device 730 for storing the program code. Storage device 730 may comprise one or more fixed disks, solid-state random-access memory, and/or removable media (e.g., a thumb drive) mounted in a corresponding interface (e.g., a Universal Serial Bus port).

Storage device 730 stores program code of control program 731. One or more processing units 722 may execute control program 731 to, in conjunction with PET system interface 723 and bed interface 725, control hardware elements to inject a radiopharmaceutical into a patient, move the patient into bore 712 past PET detectors of gantry 710, and detect coincidences occurring within the patient based on pulses generated by the PET detectors. The detected events may be stored in storage 730 as PET data 732, which may comprise raw (i.e., list-mode) data and/or sinograms. Control program 731 may also be executed to reconstruct PET images 735 based on PET data 732 using any suitable reconstruction algorithm that is or becomes known.

One or more processing units 722 may execute control program 731 to control CT imaging elements of system 700 using CT system interface 724 and bed interface 725 to acquire CT data 734. Any suitable reconstruction algorithm may be utilized to generate CT images 736 based on CT data 734. According to some embodiments, PET images 735 may be generated based at least in part on CT data 734 (e.g., using a linear attenuation coefficient map determined from CT data 734).

PET images 735 and CT images 736 may be transmitted to terminal 740 via terminal interface 726. Terminal 740 may comprise a display device and an input device coupled to system 720. Terminal 740 may display the received PET images 735 and CT images 736. Terminal 740 may receive user input for controlling display of the data, operation of system 700, and/or the processing described herein. In some embodiments, terminal 740 is a separate computing device such as, but not limited to, a desktop computer, a laptop computer, a tablet computer, and a smartphone.

Each component of system 700 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. An imaging system comprising:
- a plurality of electrical transducers, each of the plurality of electrical transducers comprising an anode and a cathode;
- a plurality of amplifiers, an input of each of the plurality of amplifiers being connected to a cathode of a respective one of the plurality of electrical transducers;
- a summation point to which an output of each of the plurality of amplifiers is connected; and
- a summing amplifier, wherein an input of the summing amplifier is connected to the summation point.

2. An imaging system according to claim 1, wherein the plurality of amplifiers are common-base amplifiers.

3. An imaging system according to claim 2, wherein a transmission line and a matching resistor are disposed between the output of each of the plurality of amplifiers and the summation point.

4. An imaging system according to claim 3, wherein each of the plurality of transmission lines exhibits a substantially similar characteristic impedance $Z_0$.

5. An imaging system according to claim 1, wherein the summing amplifier is a common-base amplifier.

6. An imaging system according to claim 1, further comprising:
- a second plurality of electrical transducers, each of the second plurality of electrical transducers comprising an anode and a cathode;
- a second plurality of amplifiers, an input of each of the second plurality of amplifiers connected to a cathode of a respective one of the second plurality of electrical transducers;
- a second summation point to which an output of each of the second plurality of amplifiers is connected; and
- a second summing amplifier, wherein an input of the second summing amplifier is connected to the second summation point.

7. An imaging system according to claim 6, further comprising:
- a first timing discrimination circuit to determine a first event time based on a signal output from an output of the summing amplifier; and
- a second timing discrimination circuit to determine a second event time based on a signal output from an output of the second summing amplifier.

8. An imaging system according to claim 7, further comprising:
- a coincidence determination unit to determine coincidences based on the first event time and the second event time.

9. A method comprising:
- receiving light photons at a plurality of electrical transducers, each of the plurality of electrical transducers comprising an anode and a cathode;
- outputting an electrical signal from each cathode of the plurality of electrical transducers in response to receipt of the light photons;
- receiving the electrical signal from each cathode at an input of a respective one of a plurality of common-base amplifiers;
- receiving output signals of the plurality of common-base amplifiers at a summation point;
- receiving the output signals from the summation point at an input of a summing amplifier;
- summing the output signals at the summing amplifier; and
- determining event times based on the summed output signals of the summing amplifier.

10. A method according to claim 9, further comprising:
- receiving second light photons at a second plurality of electrical transducers, each of the second plurality of electrical transducers comprising an anode and a cathode;
- outputting an electrical signal from each cathode of the second plurality of electrical transducers in response to receipt of the second light photons;
- receiving the electrical signal from each cathode of the second plurality of electrical transducers at an input of a respective one of a second plurality of common-base amplifiers;
- summing output signals of the second plurality of common-base amplifiers; and
- determining second event times based on the summed output signals of the second plurality of common-base amplifiers.

11. A method according to claim 10, further comprising:

determining coincidences based on the first event times and the second event times.

12. An imaging system comprising:

a plurality of electrical transducers, each of the plurality of electrical transducers comprising an anode and a cathode;

a plurality of common-base amplifiers, an input of each of the plurality of common-base amplifiers connected to a cathode of a respective one of the plurality of electrical transducers and an output of each of the plurality of common-base amplifiers connected to a respective transmission line in series with a first port of a respective matching resistor; and a summation point to which each of second ports of each of the respective matching resistors are connected; and a summing amplifier, wherein an input of the summing amplifier is connected to the summation point.

13. An imaging system according to claim 12, wherein each of the plurality of electrical transducers is to output an electrical signal in response to received light photons.

14. An imaging system according to claim 13, wherein each of the plurality of electrical transducers is a SiPM device.

15. An imaging system according to claim 12, wherein the summing amplifier is a common-base amplifier.

16. An imaging system according to claim 12, further comprising:

a second plurality of electrical transducers, each of the second plurality of electrical transducers comprising an anode and a cathode; and a second plurality of common-base amplifiers, an input of each of the second plurality of common-base amplifiers connected to a cathode of a respective one of the second plurality of electrical transducers and an output of each of the plurality of common-base amplifiers connected to a respective second transmission line in series with a first port of a respective second matching resistor; and a second summation point to which each of second ports of each of the respective second matching resistors are connected.

17. An imaging system according to claim 16, further comprising:

a first timing discrimination circuit to determine a first event time based on a signal output from the summation point; and a second timing discrimination circuit to determine a second event time based on a second signal output from the summation point.

18. An imaging system according to claim 17, further comprising:

a coincidence determination unit to determine coincidences based on the first event time and the second event time.

19. An imaging system according to claim 12, wherein each of the transmission lines exhibits a substantially similar characteristic impedance $Z_0$.

* * * * *